Aug. 7, 1956 J. H. EMERSON Re. 24,193

PRESSURE RESUSCITATOR

Original Filed Feb. 17, 1945 2 Sheets-Sheet 1

Inventor
John H. Emerson
By [illegible]
Att'ys.

PRESSURE RESUSCITATOR

Original Filed Feb. 17, 1945 2 Sheets-Sheet 2

Inventor
John H. Emerson
by Robert Cushman & Co.
Attys.

United States Patent Office

Re. 24,193
Reissued Aug. 7, 1956

24,193

PRESSURE RESUSCITATOR

John H. Emerson, Arlington, Mass.

Original No. 2,428,451, dated October 7, 1947, Serial No. 578,509, February 17, 1945. Application for reissue May 24, 1956, Serial No. 587,187

8 Claims. (Cl. 128—29)

Matter enclosed in heavy brackets [ ] appears in the original patent but forms no part of this reissue specification; matter printed in italics indicates the additions made by reissue.

This invention pertains to resuscitators, and relates more especially to a pressure resuscitator of the kind in which air or oxygen is intermittently forced into the lungs of the patient so as to inflate the lungs, the deflation of the lung depending upon the elasticity of the latter. This kind of resuscitator is much simpler and less expensive than that type wherein the lung is positively deflated by aspiration. While the aspirator type of resuscitator is doubtless to be preferred when available, the simpler pressure type is far superior, in results attained, to mere manipulative methods of resuscitation and by reason of its relative cheapness, simplicity and small size, may be made more generally available than the aspirator type.

While the pressure type of resuscitator as heretofore constructed has many desirable characteristics, it is subject in operation to one defect which in the hands of the unskilled user may lead to serious consequences. The pressure type of resuscitator is usually supplied with air or gas by means of a pump of reciprocating type (for example a bellows or a piston working in a cylinder). During the pressure stroke, the air or gas is delivered to the lungs. Usually appropriate valve means is provided which automatically closes an outlet leading from the lungs to the atmosphere during the pressure stroke and which automatically opens during the suction stroke. This arrangement in theory is wholly satisfactory, and operates as intended so long as the user continues properly to actuate the pump, but if the operator stop, particularly during or at the end of the pressure stroke, the outlet valve remains closed and if the operation is not at once resumed the patient may suffocate.

A principal object of the present invention is to provide a pressure type resuscitator having provision for automatically relieving the lung pressure whenever the reciprocating pump element is stopped during or at the end of its pressure stroke. A further object is to provide a safety release device of improved type which may be embodied in pressure resuscitators of various kinds, for example, those in which the pressure fluid is delivered to the face mask by a manually actuable bellows device rigidly connected to the mask, or in which the pressure fluid is delivered to the face mask by means of a flexible conduit from a pump or other source of intermittent pressure even though such source be remotely located. A further object is to provide a resuscitator device of simple, inexpensive type, easily operated even by an unskilled person, and of small weight and dimensions so that it is readily portable. Other and further objects and advantages of the invention will be pointed out in the following more detailed description and by reference to the accompanying drawings, wherein Fig. 1 is a side elevation illustrating a pressure resuscitator of the kind in which the pump is of bellows type, this resuscitator embodying the present invention;

Figure 1:
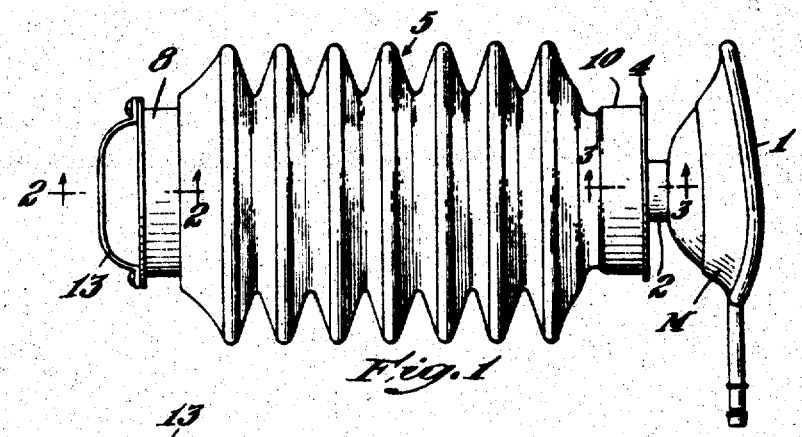

Referring to the drawings, and in particular to Figs. 1 to 4 inclusive, the face mask of the resuscitator device is indicated at M. This face mask may be of conventional type, here shown as comprising the inflatable face-engaging portion 1 and the rigid tubular stem 2 provided with the bore 3 (Fig. 3) through which the gaseous medium passes to and from the mask.

Figure 3:
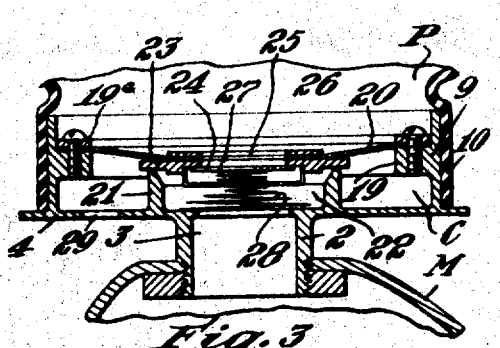
Fig. 3 is a fragmentary section to larger scale on the line 3—3 of Fig. 1.
Figure 4:
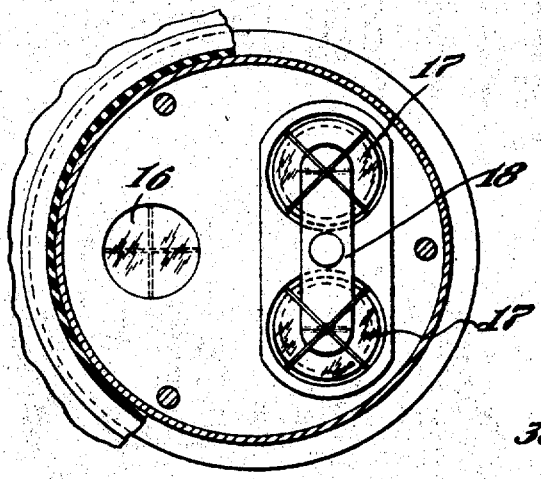
Fig. 4 is a section substantially on the line 4—4 of Fig. 2.

As illustrated in Fig. 3, this stem 2 is integral with the valve case 4, the stem and the valve case being made of any suitable material, for example metal or a moulded plastic. While as here illustrated the stem 2 and the case 4 are integrally joined, it is obviously within the invention to make them as separate parts and unite them in any appropriate way.

Figure 2:
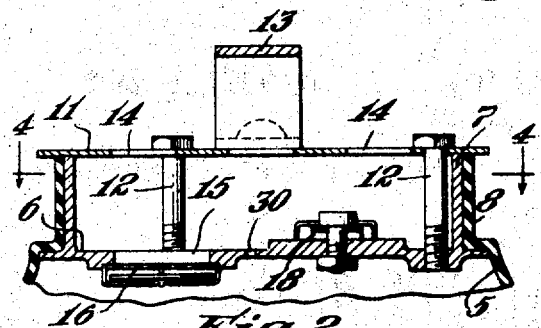
Fig. 2 is a fragmentary section to larger scale, substantially on the line 2—2 of Fig. 1.
Figure 6:
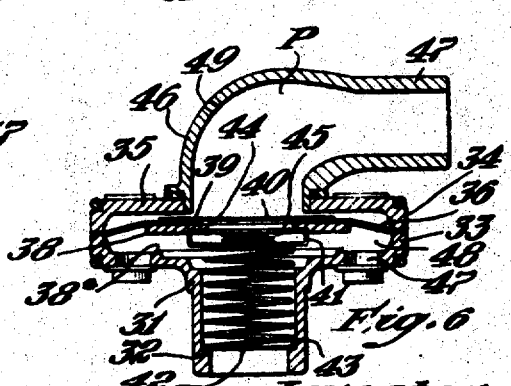
Fig. 6 is a vertical section through the device of Fig. 5, showing details of construction.

The case 4, as illustrated in Figs. 1 and 3, constitutes the normally fixed head of a pump of bellows type comprising the expansible-contractible bellows 5 of any suitable material, for instance leather, rubber, or treated textile fabric, and which is closed at its opposite end by the movable head 6 (Fig. 2). The head 6 comprises the annular cylindrical portion 7 and the bellows member 5 is provided with an elastic sleeve portion 8 which is expanded and slipped over the part 7 so as to provide a leak-tight union between the bellows member 5 and the head 6. In the same way the opposite head 4 is provided with the annular cylindrical member 9 over which the opposite sleeve portion 10 of the bellows device is drawn, the material of the bellows being sufficiently elastic to provide a leak-tight union with the opposite heads. However, if the case 4 be made of two separable parts clamped together, as illustrated in Fig. 6, the marginal portion of the bellows may be clamped, together with the margin of the diaphragm, between these casing parts.

The head 6 is preferably provided with a cover plate 11 attached to the head 6 by the bolts 12, the cover 11 being provided with a handle 13 here shown as a loop into which the operator's hand may be slipped, the cover 11 also having one or more air inlet ports 14 of large capacity.

The head 6 is furnished with a suction port 15 (Fig. 2) leading to the interior of the bellows 5. This port is controlled by an inwardly or downwardly opening valve 16. The head 6 is also furnished with one or more relief ports each normally closed by an outwardly or upwardly opening valve 17. Two such valves are here shown (Fig. 4), both valves being urged toward port closing position by means of a spring 18. This spring 18 is of such strength as to keep the valve 17 closed until a predetermined pressure has been built up in the patient's lungs, whereby these valves open automatically to avoid the application of undue pressure to the lungs. Preferably, a leak port 30 of small capacity is provided in the head 6 (Fig. 2). However, if the valves do not seat leak-tight, the leakage through the closed valves will accomplish the same result as the leak port, and the latter is not always necessary.

The casing member 4 (Fig. 3) is provided with an annular internally directed flange 19 which forms a support for the outer margin of an annular diaphragm 20, the margin of the diaphragm being clamped leak-tight to the flange 9 by a clamping ring 19a. This diaphragm, as illustrated in Fig. 3, constitutes the upper wall of a valve chamber C within which is arranged the annular valve seat 21, here shown as integral with the member 4 and coaxial with the mask stem 2. The space 22 within this valve seat 21 communicates freely with the bore 3 in the mask stem. An annular outlet valve 23 is arranged to cooperate with the seat 21, this outlet valve 23 being secured to the inner margin of the diaphragm 20 in coaxial relation with the latter. An inlet valve disk 24 is arranged to engage the under surface of the outlet valve 23 and thereby to close the inlet port 25 at the center of the valve 23. This inlet valve 24 is guided and restrained in its movements by a cage 26 extending downwardly from the lower side of the annular valve 23, and within this cage there is arranged a relatively light spring 27, which tends to keep the inlet valve 24 in closed position. A relatively heavy spring 28 reacts against the cage 26 and tends to move the diaphragm upwardly so as to separate the outlet valve 23 from the seat 21. The part 4 is provided with one or more ports 29 leading from the chamber C, surrounding the valve seat 21, to the outer atmosphere. While the springs 27 and 28, as here illustrated, are compression springs, it is contemplated that tension springs may be employed.

Figure 5:
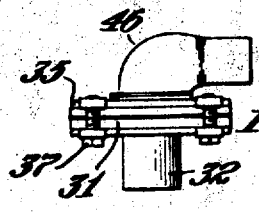
Fig. 5 is a side elevation to small scale, illustrating a modification, particularly an embodiment designed for use with a remotely located pump or other source of pulsating pressure.

A modified construction is illustrated in Figs. 5 and 6 designed for use with a pump or other source of intermittent pressure remote from the face mask. In this arrangement there is provided a casing member 31 here shown as integral with the tubular stem 32 to which the face mask may be secured in any desired manner. The part 31 is provided with an annular upstanding wall 33, with which cooperates the downwardly directed annular wall 34 of the upper member 35 of the valve case, the parts 33 and 34 clamping the outer margin of an annular diaphragm 36 between them. The parts 31 and 35 are united by suitable bolts 37 (Fig. 5) to form a leak-tight casing.

The annular outlet valve 38 is secured by means of a clamping plate 39 to the inner margin of the diaphragm 36. This annular valve 38 cooperates with an annular valve seat 38a, here shown as integral with the part 31 and coaxial with the member 32. The aperture 40 at the center of the valve 38 constitutes an inlet port leading from the upper part of the casing to the bore in the part 32. A valve-guiding cage 41 extends downwardly from the valve 38 and is engaged by a relatively heavy spring 42 whose lower end abuts a shoulder 43 at the interior of the part 32, this spring urging the valve 38 away from the seat 38a. Within the guiding cage 41 there is arranged an inlet valve disk 44 which cooperates with the inner margin of the valve 38 to close the passage 40, a relatively light spring 45 reacting between the cage 41 and the valve disk and tending to keep the valve disk 44 in closed position.

To the part 35 of the valve case there is secured leak-tight an elbow 46 having the nipple portion 47 designed to receive the end of a flexible hose leading from a suitable pump or other source of intermittently applied pressure. The lower member 31 of the valve case is provided with one or more ports 47 of large capacity leading from the space 48, beneath the diaphragm 36 and surrounding the valve seat 38a to the outer atmosphere, and the part 46 is furnished with a leak port 49 of small capacity.

A further modification is illustrated in Figs. 7 to 11 inclusive wherein the mask M is shown associated with a pump of the reciprocating piston type. In this arrangement the mask M is furnished with the tubular rigid stem 50 which is here illustrated (Fig. 9) as integrally joined to the lower member 51 of the valve casing. The peripheral wall of this valve casing is furnished with an inwardly directed flange 52 forming a support for the outer margin of the flexible diaphragm 53. The lower member of the casing is also furnished with an annular valve seat 54 coaxial with the stem member 50 and with which cooperates the annular outlet valve 55 which is secured to the inner margin of the diaphragm 53 in coaxial relation with the seat 54. A relatively heavy spring 56 engages the valve 55 and urges the latter away from the seat 54. The valve 55 has the central port 57 (Fig. 9) providing for passage of fluid from the plenum chamber P above the diaphragm to the space inside the valve seat 54, and an inlet valve disk 58 is arranged so that it tends to close this port 57, the valve being urged toward port-closing position by a relatively light spring 59 which is anchored to a part 60 secured to the outlet valve 55. The term "plenum chamber" as thus applied to the space within the apparatus and above the diaphragm, is used merely for convenience in distinguishing among the various spaces and cavities and is intended to designate that space in which during inhalation (but not necessarily during exhalation) a superatmospheric pressure subsists and from which during inhalation gaseous medium passes through the inlet valve to the face mask and lungs.

Figure 7:
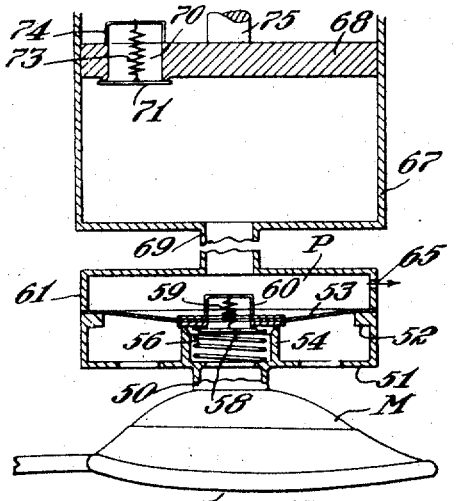
Fig. 7 is a fragmentary vertical section illustrating a further embodiment of the invention, and showing a reciprocating pump as the device for providing the pulsating pressure, the pump piston being shown at the beginning of its pressure stroke.
Figure 8:
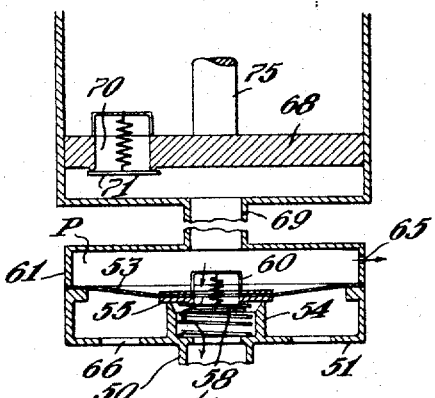
Fig. 8 is a view similar to Fig. 7, but showing the pump piston nearing the end of its pressure stroke, and indicating the position of the inlet and outlet valves of the resuscitator at this time.
Figure 9:
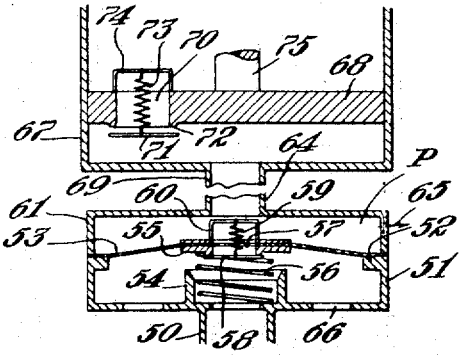
Fig. 9 is a view similar to Fig. 8, but showing the position which the parts occupy just after the pump piston begins the upstroke.

The valve casing also comprises the upper member 61 which is connected to the part 51 in any appropriate way, for example by bolts (not shown), the margin of the diaphragm 53 being clamped leak-tight between the opposed portions of the casing members 51 and 61. The upper member 61 of the case is furnished with a tubular stem or nipple 64 and is provided with a leak port 65 of small capacity. The lower member 51 of the case is also furnished with one or more ports 66 of large capacity leading from the space beneath the diaphragm and surrounding the valve seat 54 to the outer atmosphere. As here illustrated, the pressure fluid is supplied to the valve casing by means of a pump comprising the cylinder 67 and the reciprocating piston 68, the cylinder being provided with a delivery nipple 69 which may be integral with the member 64 of the valve casing or which may be connected to the latter in any desired manner, and at any appropriate distance from the valve casing. As illustrated, the piston 68 is provided with a port 70 which is controlled by a valve 71 cooperable with an annular seat 72 (Fig. 9) the valve 71 being urged toward the seat by a spring 73 anchored to a support 74 carried by the piston. The piston is reciprocated by means of a piston rod 75 (Fig. 8) which may be actuated by hand or by power, as desired. The operation of the device as illustrated in Figs. 7 to 11 is substantially as follows:

As shown in Fig. 7 a piston 68 has completed its upstroke and has started down with its valve 71 seated. When the piston starts down the gaseous medium within the cylinder is compressed, the diaphragm is forced down so as to seat valve 55, and as the pressure further increases the inlet valve 58 is moved away from its seat; the gaseous medium from plenum chamber P now passes down through the open inlet port 57 and into the tubular member 50, as indicated by the arrows (Fig. 8) and then into the face mask. Some of the gaseous medium also escapes to the atmosphere through the leak port 55. If, as is intended, the pump piston 68 begins its return or suction stroke without pause, the parts assume the relative positions shown in Fig. 9, the valve 71 in the piston opening to admit air to the space within the pump cylinder beneath the piston, the inlet valve 58 closing, and the diaphragm 53 rising in response both to the suction and to the action of the spring 56, thereby providing free communication between the interior of the tubular stem 50 and the space beneath the diaphragm and outside of the valve seat 54. The natural elasticity of the lung now causes the lung to contract, forcing out the air from the lung through the face mask, through the stem 50, over the edge of the valve seat 54, and out through the ports 66. This action continues until the piston 68 reaches the upper end of its path of travel, thus completing the cycle.

Figure 10:
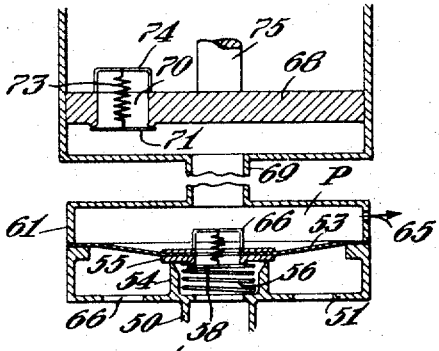
Fig. 10 is a view similar to Fig. 8, but indicating the position which the parts occupy when the pump piston is at the lowermost portion of its pressure stroke and just before it starts its upward stroke.
Figure 11:
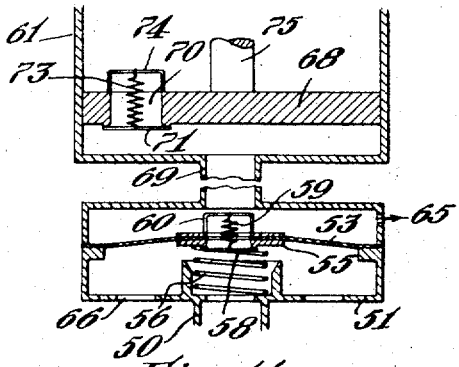
Fig. 11 is a view similar to Fig. 10 but showing the position which the parts assume if the pump piston is left standing at the lower end of its pressure stroke.

If, instead of starting back on its suction stroke immediately after completing or partially completing its pressure stroke, the piston should become stationary with superatmospheric pressure still subsisting in chamber P, the parts would for the instant occupy the positions shown in Fig. 10, all of the several valves being closed. With the parts in this position the gaseous medium is under some degree of pressure within the plenum chamber P above the diaphragm, but the lung cavity is completely cut off from the outside atmosphere and there is no way for the air from the lung to escape. However, by the provision of the leak port 68, the pressure in the plenum chamber above the diaphragm (said chamber being of small capacity) begins immediately to drop, since the piston 68 is now stationary. As soon as the pressure in the chamber P has dropped even to a very slight degree, the diaphragm 53 is unable longer to resist the upward urge of the spring 56 and thus the latter raises the outlet valve 55 from the seat 54, as shown in Fig. 11, providing free communication between the lung cavity and the outer atmosphere. Thus, with this arrangement, there is no possibility that the patient may be suffocated by failure of the operator to actuate the pump piston in the proper way.

The operation of the devices shown in Figs. 1 to 6 will be obvious, it is believed, from the above description with respect to Figs. 7 to 11. Thus in the arrangement shown in Figs. 1 to 4 inclusive, the pressure stroke of the upper head 6 of the bellows device first forces the diaphragm down so as to seat valve 23, the valve 24 also being seated. As the pressure in chamber P further increases the valve 24 is unseated. Air from the plenum chamber P (constituted by the interior of the bellows) thus enters the lung through the face mask. On the reverse or suction stroke of the bellows, the valve 24 is closed and the spring 28 raises the valve 23 from its seat. This is the normal operation of the device. If the operator should hold the bellows collapsed, the air from the plenum chamber P, that is to say, the interior of the bellows, gradually leaks out through the leak port 30 in the upper head 6 of the bellows, and, when the pressure has been reduced very slightly, the spring 28 raises the valve 23 from its seat 21, thus providing free communication between the face mask and the chamber C and the outer atmosphere.

The device shown in Fig. 6 operates in substantially the same manner, it being assumed that pressure is built up intermittently in the plenum chamber P within the member 46. As the pressure builds up the diaphragm is depressed, seating valve 38. As the pressure further increases the valve 44 is unseated and the gaseous medium from the chamber P passes through the orifice 40 and through the tubular member 32 to the face mask. When the pressure pulsation ceases and a suction impulse begins, the diaphragm 36 rises and unseats the valve 38. If no suction impulse occurs, following a given pressure impulse, the pressure medium contained within the chamber P quickly leaks through the leak port 49 thus reducing the pressure in the chamber P and permitting the spring 42 to raise the annular outlet valve 38 from the seat 38*a*.

While certain desirable embodiments of the invention have been illustrated and described by way of example, it is to be understood that the invention is broadly inclusive of any and all modifications and equivalent constructions falling within the scope of the appended claims.

I claim:

1. In a resuscitator of the type having a face mask, a plenum chamber wherein a gaseous medium under pressure is periodically supplied, means providing communication between the interior of the plenum chamber and the interior of the mask and first valve means adpated to open said communication when the pressure in the plenum chamber attains a predetermined amount and to close said communication when it falls below a predetermined amount, the improvement comprising a valve chamber, means providing free communication between the atmosphere and the interior of the face mask through said valve chamber, a diaphragm moveable in response to variations in pneumatic pressure and forming a wall between the plenum chamber and the valve chamber, said diaphragm being constructed and arranged to move inwardly of the valve chamber when the pressure in the plenum chamber attains a predetermined amount and to move outwardly of the valve chamber when the pressure in the plenum chamber falls below a predetermined amount, a second valve means mounted on said diaphragm and adapted to close said communication between the atmosphere and the interior of the face mask when the diaphragm is moved inwardly of the valve chamber and to open said communication when the diaphragm is moved outwardly of the valve chamber and means providing a relatively slow leakage from the plenum chamber to the atmosphere, whereby upon discontinuing the supply of gaseous medium under pressure to the interior of the plenum chamber for a predetermined interval the pressure in the plenum chamber is automatically reduced by said slow leakage, the pressure-responsive diaphragm automatically moves outwardly of the valve chamber in response to said reduced pressure and said second valve opens said free communication between the atmosphere and the interior of the face mask through the valve chamber.

2. In a resuscitator of the type having a face mask, a plenum chamber wherein a gaseous medium under pressure is periodically supplied, means providing communication between the interior of the plenum chamber and the interior of the mask and first valve means adapted to open said communication when the pressure in the plenum chamber attains a predetermined amount and to close said communication when it falls below a predetermined amount, the improvement comprising a valve chamber, means providing free communication between the atmosphere and the interior of the face mask through said valve chamber, a diaphragm moveable in response to variations in pneumatic pressure and forming a wall between the plenum chamber and the valve chamber, said diaphragm being constructed and arranged to move inwardly of the valve chamber when the pressure in the plenum chamber attains a predetermined amount and to move outwardly of the valve chamber when the pressure in the plenum chamber falls below a predetermined amount, a mechanical guard means constructed and arranged to maintain at all times a free space to accommodate outward movement of said diaphragm, a second valve means mounted on said diaphragm and adapted to close said communication between the atmosphere and the interior of the face mask when the diaphragm is moved inwardly of the valve chamber and to open said communication when the diaphragm is moved outwardly of the valve chamber and means providing a relatively slow leakage from the plenum chamber to the atmosphere, whereby upon discontinuing the supply of gaseous medium under pressure to the interior of the plenum chamber for a predetermined interval the pressure in the plenum chamber is automatically reduced by said slow leakage, the pressure-responsive diaphragm automatically moves outwardly of the valve chamber in response to said reduced pressure and said second valve opens said free communication between the atmosphere and the interior of the face mask through the valve chamber.

3. In a resuscitator of the type having a face mask and a plenum chamber wherein a gaseous medium under pressure is periodically supplied, the improvement comprising a valve chamber, means providing free communication between the atmosphere and the interior of the valve chamber, means providing free communication between the interior of the face mask and said valve chamber, a diaphragm moveable in response to variations in pneumatic pressure and forming a wall between the plenum chamber and the valve chamber, said diaphragm being constructed and arranged to move inwardly of the valve chamber when the pressure in the plenum chamber attains a predetermined amount and to move outwardly of the valve chamber when the pressure in the plenum chamber falls below a predetermined amount, a mechanical guard means constructed and arranged to maintain a free space to accommodate outward movement of said diaphragm, a first valve means mounted on said diaphragm and adapted to close said free communication between the atmosphere and the interior of the valve chamber when the diaphragm is moved inwardly of the valve chamber and to open said communication when the diaphragm is moved outwardly of the valve chamber, a port in said diaphragm providing communication between the plenum chamber and said valve chamber, a second valve means adapted to close said port, a relatively light spring urging the second valve means toward closed position and a leak port in said plenum chamber providing a relatively slow leakage from the plenum chamber to the atmosphere, whereby upon discontinuing the supply of gaseous medium under pressure to the interior of the plenum chamber for a predetermined interval the pressure in the plenum chamber is automatically reduced by said slow leakage, the pressure-response diaphragm automatically moves outwardly of the valve chamber in response to said reduced pressure and said first valve means opens said free communication between the atmosphere and the interior of the valve chamber.

4. In a resuscitator of the type having a face mask, a plenum chamber wherein a gaseous medium under pressure is periodically supplied by a pump having a reciprocating part, means providing communication between the interior of the plenum chamber and the interior of the mask and first valve means adapted to open said communication when the pressure in the plenum chamber attains a predetermined amount and to close said communication when it falls below a predetermined amount, the improvement comprising a valve chamber, means providing free communication between the atmosphere and the interior of the face mask through said valve chamber, a diaphragm moveable in response to variations in pneumatic pressure and forming a wall between the plenum chamber and the valve chamber, said diaphragm being constructed and arranged to move inwardly of the valve chamber when the pressure in the plenum chamber attains a predetermined amount and to move outwardly of the valve chamber when the pressure in the plenum chamber falls below a predetermined amount, a mechanical guard means constructed and arranged to maintain a free space for outward movement of said diaphragm; a second valve means mounted on said diaphragm and adapted to close said communication between the atmosphere and the interior of the face mask when the diaphragm is moved inwardly of the valve chamber and to open said communication when the diaphragm is moved outwardly of the valve chamber and means providing a relatively slow leakage from the plenum chamber to the atmosphere, whereby upon discontinuing the supply of gaseous medium under pressure to the interior of the plenum chamber for a predetermined interval, the pressure in the plenum chamber is automatically reduced, the pressure-responsive diaphragm automatically moves outwardly of the valve chamber in response to said reduced pressure and said second valve means opens said free communication between the atmosphere and the interior of the face mask through the valve chamber.

5. In a resuscitator of the type having a face mask, a plenum chamber wherein a gaseous medium under pressure is periodically supplied by contraction and expansion of the plenum chamber, means providing communication between the interior of the plenum chamber and the interior of the mask and first valve means adapted to open said communication when the pressure in the plenum chamber attains a predetermined amount and to close said communication when it falls below a predetermined amount, the improvement comprising a valve chamber, means providing free communication between the atmosphere and the interior of the face mask through said valve chamber, a diaphragm movable in response to variations in pneumatic pressure and forming a wall between the plenum chamber and the valve chamber, said diaphragm being constructed and arranged to move inwardly of the valve chamber when the pressure in the plenum chamber attains a predetermined amount and to move outwardly of the valve chamber when the pressure in the plenum chamber falls below a predetermined amount, a mechanical guard means constructed and arranged to maintain at all times a free space to accommodate outward movement of said diaphragm and second valve means mounted on said diaphragm and adapted to close said communication between the atmosphere and the interior of the face mask when the diaphragm is moved inwardly of the valve chamber and to open said communication when the diaphragm is moved outwardly of the valve chamber and means providing a relatively slow leakage from the plenum chamber to the atmosphere, whereby upon discontinuing the supply of gaseous medium under pressure to the interior of the plenum chamber for a predetermined interval the pressure in the plenum chamber is automatically reduced by said slow leakage, the pressure-responsive diaphragm automaticall moves outwardly of the valve chamber in response to said reduced pressure and said second valve means opens said free communication between the atmosphere and the interior of the face mask through the valve chamber.

6. In a resuscitator of the type having a face mask, a plenum chamber wherein a gaseous medium under pressure is periodically supplied, means providing communication between the interior of the plenum chamber and the interior of the mask and first valve means adapted to open said communication when the pressure in the plenum chamber attains a predetermined amount and to close said communication when it falls below a predetermined amount, the improvement comprising a valve chamber, means providing free communication between the atmosphere and the interior of the face mask through said valve chamber, a diaphragm moveable in response to variations in pneumatic pressure and forming a wall between the plenum chamber and the valve chamber and a second valve means mounted on said diaphragm and adapted to close said communication between the atmosphere and the interior of the face mask when the diaphragm is moved inwardly of the valve chamber and to open said communication when the diaphragm is moved outwardly of the valve chamber, whereby the pressure-responsive diaphragm automatically moves outwardly of the valve chamber in response to reduced pressure in the plenum chamber causing said second valve to open said free communication between the atmosphere and the interior of the face mask during the exhalation phase of resuscitation and the pressure-responsive diaphragm automatically moves inwardly of the valve chamber causing said second valve means to close said free communication during the [exhalation] *inhalation* phase of resuscitation.

7. In a resuscitator of the type having a face mask, a plenum chamber wherein a gaseous medium under pressure is periodically supplied, means providing communication between the interior of the plenum chamber and the interior of the mask and first valve means adapted to open said communication when the pressure in the plenum chamber attains a predetermined amount and to close said communication when it falls below a predetermined amount, the improvement comprising a valve chamber, means providing free communication between the atmosphere and the interior of the face mask through said valve chamber, a diaphragm moveable in response to variations in pneumatic pressure and forming a wall between the plenum chamber and the valve chamber, a mechanical guard means constructed and arranged to maintain at all times a free space to accommodate outward movement of said diaphragm and a second valve means mounted on said diaphragm and adapted to close said communication between the atmosphere and the interior of the face mask when the diaphragm is moved inwardly of the valve chamber and to open said communication when the diaphragm is moved outwardly of the valve chamber, whereby the pressure-responsive diaphragm automatically moves outwardly of the valve chamber in response to reduced pressure in the plenum chamber causing said second valve to open said free communication between the atmosphere and the interior of the face mask during the exhalation phase of resuscitation and the pressure-responsive diaphragm automatically moved inwardly of the valve chamber causing said second valve means to close said free communication during the [exhalation] *inhalation* phase of resuscitation.

8. In a resuscitator of the type having a face mask and a plenum chamber wherein a gaseous medium under pressure is periodically supplied, the improvement comprising a valve chamber, means providing free communication between the atmosphere and the interior of the valve chamber, means providing free communication between the interior of the face mask and said valve chamber, a diaphragm moveable in response to variations in pneumatic pressure and forming a wall between the plenum chamber and the valve chamber, a mechanical guard means constructed and arranged to maintain a free space to accommodate outward movement of said diaphragm, a first valve means mounted on said diaphragm and adapted to close said free communication between the atmosphere and the interior of the valve chamber when the diaphragm is moved inwardly of the valve chamber and to open said communication when the diaphragm is moved outwardly of the valve chamber, a port in said diaphragm providing communication between the plenum chamber and said valve chamber, a second valve means adapted to close said port and a relatively light spring urging the second valve means toward closed position, whereby the pressure-responsive diaphragm automatically moves outwardly of the valve chamber in response to reduced pressure in the plenum chamber causing said first valve means to open said free communication between the atmosphere and the interior of the face mask during the exhalation phase of resuscitation and the pressure-responsive diaphragm automatically moves inwardly of the valve chamber causing said first valve means to close said free communication during the [exhalation] *inhalation* phase of resuscitation.

References Cited in the file of this patent or the original patent

UNITED STATES PATENTS

| | | |
|---|---|---|
| 1,157,655 | Mayer et al. | Oct. 19, 1915 |
| 1,172,879 | Davis | Feb. 22, 1916 |
| 1,197,232 | Pierpont | Sept. 5, 1916 |
| 1,202,125 | Tullar | Oct. 24, 1916 |
| 2,399,643 | Kreiselman | May 7, 1946 |

OTHER REFERENCES

"A New Resuscitation Apparatus," Joseph Kreiselman, Anesthesiology, vol. 4, November 1943, pp. 608 to 611.